(12) United States Patent
Gilbert

(10) Patent No.: US 8,207,651 B2
(45) Date of Patent: Jun. 26, 2012

(54) LOW ENERGY OR MINIMUM DISTURBANCE METHOD FOR MEASURING FREQUENCY RESPONSE FUNCTIONS OF ULTRASONIC SURGICAL DEVICES IN DETERMINING OPTIMUM OPERATING POINT

(75) Inventor: James A. Gilbert, Boulder, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 365 days.

(21) Appl. No.: 12/561,067

(22) Filed: Sep. 16, 2009

(65) Prior Publication Data
US 2011/0066174 A1 Mar. 17, 2011

(51) Int. Cl.
*H01L 41/08* (2006.01)
(52) U.S. Cl. .................................. 310/317; 310/316.01
(58) Field of Classification Search ............ 310/316.01, 310/317, 318, 319; 318/116–118
See application file for complete search history.

(56) References Cited

U.S. PATENT DOCUMENTS

| | | |
|---|---|---|
| 4,052,987 A | 10/1977 | Wuchinich et al. |
| 4,063,557 A | 12/1977 | Wuchinich et al. |
| 4,193,818 A | 3/1980 | Young et al. |
| 4,223,676 A | 9/1980 | Wuchinich et al. |
| 4,319,580 A | 3/1982 | Colley et al. |
| 4,354,502 A | 10/1982 | Colley et al. |
| 4,412,288 A | 10/1983 | Herman |
| 4,425,115 A | 1/1984 | Wuchinich |
| 4,493,694 A | 1/1985 | Wuchinich |
| 4,516,398 A | 5/1985 | Wuchinich |
| 4,526,571 A | 7/1985 | Wuchinich |
| 4,589,078 A | 5/1986 | Rosenberg |
| 4,646,754 A | 3/1987 | Seale |
| 4,750,488 A | 6/1988 | Wuchinich et al. |
| 4,750,901 A | 6/1988 | Molteno |
| 4,750,902 A | 6/1988 | Wuchinich et al. |
| 4,763,282 A | 8/1988 | Rosenberg |
| 4,771,792 A | 9/1988 | Seale |
| 4,787,247 A | 11/1988 | Wuchinich et al. |
| 4,827,911 A | 5/1989 | Broadwin et al. |
| 4,851,816 A | 7/1989 | Macias et al. |
| 4,921,476 A | 5/1990 | Wuchinich |
| 4,922,902 A | 5/1990 | Wuchinich et al. |
| 4,930,512 A | 6/1990 | Henriksen et al. |
| 4,931,047 A | 6/1990 | Broadwin et al. |

(Continued)

FOREIGN PATENT DOCUMENTS

EP 1495727 A2 1/2005

(Continued)

OTHER PUBLICATIONS

European Search Report dated Jul. 1, 2011 from counterpart European Application No. 10177202.8.

*Primary Examiner* — Mark Budd

(57) ABSTRACT

An ultrasonic system is provided that includes an ultrasonic device having an elongated member configured to impart ultrasonic energy to tissue and a resonator configured to impart a frequency to the elongated member. The system also includes an ultrasonic generator configured to supply power to the resonator of the ultrasonic device. The ultrasonic generator has a drive signal generator configured to provide a drive signal, a noise signal generator configure to provide a noise signal, and a controller. The controller receives an output signal from the ultrasonic device and the noise signal from the noise signal generator, calculates a transfer function based on the output signal and the noise signal, and adjusts the drive signal generator based on the calculated transfer function.

3 Claims, 11 Drawing Sheets

U.S. PATENT DOCUMENTS

| | | |
|---|---|---|
| 5,011,608 A | 4/1991 | Damjanovic |
| 5,015,227 A | 5/1991 | Broadwin et al. |
| 5,026,387 A | 6/1991 | Thomas |
| 5,045,054 A | 9/1991 | Hood et al. |
| 5,057,182 A | 10/1991 | Wuchinich |
| 5,151,085 A | 9/1992 | Sakurai et al. |
| 5,167,619 A | 12/1992 | Wuchinich |
| 5,171,387 A | 12/1992 | Wuchinich |
| 5,176,677 A | 1/1993 | Wuchinich |
| 5,221,282 A | 6/1993 | Wuchinich |
| 5,222,600 A | 6/1993 | Stoddard et al. |
| 5,241,964 A | 9/1993 | McQuilkin |
| 5,249,121 A | 9/1993 | Baum et al. |
| 5,269,289 A | 12/1993 | Takehana et al. |
| 5,284,484 A | 2/1994 | Hood et al. |
| 5,300,021 A | 4/1994 | Wuchinich |
| 5,312,329 A | 5/1994 | Beaty et al. |
| 5,322,055 A | 6/1994 | Davison et al. |
| RE34,663 E | 7/1994 | Seale |
| 5,330,481 A | 7/1994 | Hood et al. |
| 5,334,183 A | 8/1994 | Wuchinich |
| 5,358,505 A | 10/1994 | Wuchinich |
| 5,417,246 A | 5/1995 | Perkins et al. |
| 5,425,704 A | 6/1995 | Sakurai et al. |
| 5,428,223 A | 6/1995 | Jatteau et al. |
| 5,462,522 A | 10/1995 | Sakurai et al. |
| 5,466,020 A | 11/1995 | Page et al. |
| 5,484,398 A | 1/1996 | Stoddard |
| 5,543,831 A | 8/1996 | Tsuji et al. |
| 5,545,223 A | 8/1996 | Neuenfeldt et al. |
| 5,549,139 A | 8/1996 | Perkins et al. |
| 5,560,360 A | 10/1996 | Filler et al. |
| 5,591,344 A | 1/1997 | Kenley et al. |
| 5,627,584 A | 5/1997 | Nishikori et al. |
| 5,630,935 A | 5/1997 | Treu |
| 5,645,734 A | 7/1997 | Kenley et al. |
| 5,651,893 A | 7/1997 | Kenley et al. |
| 5,658,456 A | 8/1997 | Kenley et al. |
| 5,670,050 A | 9/1997 | Brose et al. |
| 5,674,390 A | 10/1997 | Matthews et al. |
| 5,674,397 A | 10/1997 | Pawlak et al. |
| 5,674,404 A | 10/1997 | Kenley et al. |
| 5,690,821 A | 11/1997 | Kenley et al. |
| 5,690,831 A | 11/1997 | Kenley et al. |
| 5,702,606 A | 12/1997 | Peter, Jr. et al. |
| 5,705,066 A | 1/1998 | Treu et al. |
| 5,707,086 A | 1/1998 | Treu et al. |
| 5,713,888 A | 2/1998 | Neuenfeldt et al. |
| 5,714,060 A | 2/1998 | Kenley et al. |
| 5,716,531 A | 2/1998 | Kenley et al. |
| 5,725,776 A | 3/1998 | Kenley et al. |
| 5,730,720 A | 3/1998 | Sites et al. |
| 5,733,336 A | 3/1998 | Neuenfeldt et al. |
| 5,762,609 A | 6/1998 | Benaron et al. |
| 5,762,782 A | 6/1998 | Kenley et al. |
| 5,783,072 A | 7/1998 | Kenley et al. |
| 5,786,691 A | 7/1998 | Palmer, Jr. et al. |
| 5,797,849 A | 8/1998 | Vesely et al. |
| 5,810,859 A | 9/1998 | DiMatteo et al. |
| 5,811,909 A | 9/1998 | Wuchinich |
| 5,830,848 A | 11/1998 | Harrison et al. |
| 5,844,140 A | 12/1998 | Seale |
| 5,853,005 A | 12/1998 | Scanlon |
| 5,855,553 A | 1/1999 | Tajima et al. |
| 5,857,485 A | 1/1999 | Perkins et al. |
| 5,863,421 A | 1/1999 | Peter, Jr. et al. |
| 5,891,131 A | 4/1999 | Rajan et al. |
| 5,924,991 A | 7/1999 | Hossack et al. |
| 5,928,151 A | 7/1999 | Hossack et al. |
| 5,958,782 A | 9/1999 | Bentsen et al. |
| 5,979,494 A | 11/1999 | Perkins et al. |
| 5,989,275 A | 11/1999 | Estabrook et al. |
| 6,017,307 A | 1/2000 | Raines et al. |
| 6,019,724 A | 2/2000 | Gronningsaeter et al. |
| 6,019,725 A | 2/2000 | Vesely et al. |
| 6,086,369 A | 7/2000 | Sharp et al. |
| 6,099,457 A | 8/2000 | Good |
| 6,122,042 A | 9/2000 | Wunderman et al. |
| 6,141,588 A | 10/2000 | Cox et al. |
| 6,149,587 A | 11/2000 | Raines |
| 6,161,032 A | 12/2000 | Acker |
| 6,166,496 A | 12/2000 | Lys et al. |
| 6,192,752 B1 | 2/2001 | Blaine et al. |
| 6,200,266 B1 | 3/2001 | Shokrollahi et al. |
| 6,211,626 B1 | 4/2001 | Lys et al. |
| 6,214,017 B1 | 4/2001 | Stoddard et al. |
| 6,219,575 B1 | 4/2001 | Nemati |
| 6,231,834 B1 | 5/2001 | Unger et al. |
| 6,232,107 B1 | 5/2001 | Bryan et al. |
| 6,246,898 B1 | 6/2001 | Vesely et al. |
| 6,256,859 B1 | 7/2001 | Stoddard et al. |
| 6,261,235 B1 | 7/2001 | Amano et al. |
| 6,290,685 B1 | 9/2001 | Insley et al. |
| 6,292,901 B1 | 9/2001 | Lys et al. |
| 6,312,393 B1 | 11/2001 | Abreu |
| 6,317,619 B1 | 11/2001 | Boernert et al. |
| 6,319,197 B1 | 11/2001 | Tsuji et al. |
| 6,325,811 B1 | 12/2001 | Messerly |
| 6,330,464 B1 | 12/2001 | Colvin, Jr. et al. |
| 6,334,849 B1 | 1/2002 | Sunagawa |
| 6,340,868 B1 | 1/2002 | Lys et al. |
| 6,364,835 B1 | 4/2002 | Hossack et al. |
| 6,364,842 B1 | 4/2002 | Amano et al. |
| 6,413,233 B1 | 7/2002 | Sites et al. |
| 6,420,622 B1 | 7/2002 | Johnston et al. |
| 6,436,682 B1 | 8/2002 | Bryan et al. |
| 6,459,919 B1 | 10/2002 | Lys et al. |
| 6,468,265 B1 | 10/2002 | Evans et al. |
| 6,511,478 B1 | 1/2003 | Burnside et al. |
| 6,516,665 B1 | 2/2003 | Varadan et al. |
| 6,521,211 B1 | 2/2003 | Unger et al. |
| 6,528,954 B1 | 3/2003 | Lys et al. |
| 6,544,193 B2 | 4/2003 | Abreu |
| 6,554,770 B1 | 4/2003 | Sumanaweera et al. |
| 6,562,001 B2 | 5/2003 | Lebel et al. |
| 6,571,128 B2 | 5/2003 | Lebel et al. |
| 6,577,080 B2 | 6/2003 | Lys et al. |
| 6,577,899 B2 | 6/2003 | Lebel et al. |
| 6,582,387 B2 | 6/2003 | Derek et al. |
| 6,613,280 B2 | 9/2003 | Myrick et al. |
| 6,618,612 B1 | 9/2003 | Acker et al. |
| 6,622,542 B2 | 9/2003 | Derek et al. |
| 6,641,536 B2 | 11/2003 | Hossack et al. |
| 6,648,821 B2 | 11/2003 | Lebel et al. |
| 6,654,999 B2 | 12/2003 | Stoddard et al. |
| 6,656,133 B2 | 12/2003 | Voegele et al. |
| 6,666,811 B1 | 12/2003 | Good |
| 6,666,835 B2 | 12/2003 | Martin et al. |
| 6,668,196 B1 | 12/2003 | Villegas et al. |
| 6,669,633 B2 | 12/2003 | Brodsky et al. |
| 6,673,596 B1 | 1/2004 | Sayler et al. |
| 6,709,526 B1 | 3/2004 | Bailey et al. |
| 6,711,423 B2 | 3/2004 | Colvin, Jr. et al. |
| 6,720,745 B2 | 4/2004 | Lys et al. |
| 6,740,075 B2 | 5/2004 | Lebel et al. |
| 6,767,329 B2 | 7/2004 | Amano et al. |
| 6,773,444 B2 | 8/2004 | Messerly |
| 6,783,493 B2 | 8/2004 | Chiang et al. |
| 6,808,508 B1 | 10/2004 | Zafirelis et al. |
| 6,810,290 B2 | 10/2004 | Lebel et al. |
| 6,832,735 B2 | 12/2004 | Yadav et al. |
| 6,843,099 B2 | 1/2005 | Derek et al. |
| 6,855,337 B1 | 2/2005 | Nelson et al. |
| 6,857,746 B2 | 2/2005 | Dyner et al. |
| 6,858,003 B2 | 2/2005 | Evans et al. |
| 6,866,659 B2 | 3/2005 | Nemati |
| 6,867,342 B2 | 3/2005 | Johnston et al. |
| 6,873,268 B2 | 3/2005 | Lebel et al. |
| 6,877,975 B2 | 4/2005 | Wuchinich |
| 6,958,705 B2 | 10/2005 | Lebel et al. |
| 6,960,894 B2 | 11/2005 | Carusillo et al. |
| 6,969,352 B2 | 11/2005 | Chiang et al. |
| 6,970,741 B1 | 11/2005 | Whitehurst et al. |
| 6,970,742 B2 | 11/2005 | Mann et al. |
| 6,974,435 B2 | 12/2005 | Daw et al. |
| 6,974,437 B2 | 12/2005 | Lebel et al. |
| 6,976,969 B2 | 12/2005 | Messerly |

| | | | | | | |
|---|---|---|---|---|---|---|
| 6,979,329 | B2 | 12/2005 | Burnside et al. | 7,338,637 B2 | 3/2008 | Pease et al. |
| 6,982,146 | B1 | 1/2006 | Schneider et al. | 7,344,493 B2 | 3/2008 | Sonnenschein et al. |
| 6,984,220 | B2 | 1/2006 | Wuchinich | 7,350,936 B2 | 4/2008 | Ducharme et al. |
| 6,984,332 | B2 | 1/2006 | Varadan et al. | 7,352,339 B2 | 4/2008 | Morgan et al. |
| 6,986,739 | B2 | 1/2006 | Warren et al. | 7,354,584 B2 | 4/2008 | Reed et al. |
| 7,007,872 | B2 | 3/2006 | Yadav et al. | 7,357,035 B2 | 4/2008 | Liu et al. |
| 7,010,356 | B2 | 3/2006 | Jog et al. | 7,374,552 B2 | 5/2008 | Wuchinich |
| 7,013,703 | B2 | 3/2006 | Derek et al. | 7,387,405 B2 | 6/2008 | Ducharme et al. |
| 7,014,336 | B1 | 3/2006 | Ducharme et al. | 7,403,805 B2 | 7/2008 | Abreu |
| 7,016,714 | B2 | 3/2006 | Colvin, Jr. | 7,405,289 B2 | 7/2008 | Johnson et al. |
| 7,018,333 | B2 | 3/2006 | Wang et al. | 7,422,568 B2 | 9/2008 | Yang et al. |
| 7,037,428 | B1 | 5/2006 | Robinson et al. | 7,422,582 B2 | 9/2008 | Malackowski et al. |
| 7,038,398 | B1 | 5/2006 | Lys et al. | 7,435,232 B2 | 10/2008 | Liebschner |
| 7,041,063 | B2 | 5/2006 | Abreu | 7,453,217 B2 | 11/2008 | Lys et al. |
| 7,041,369 | B1 | 5/2006 | Mackey et al. | 7,455,973 B2 | 11/2008 | Fischer et al. |
| 7,048,756 | B2 | 5/2006 | Eggers et al. | 7,465,274 B2 | 12/2008 | Amano et al. |
| 7,066,781 | B2 | 6/2006 | Weston | 7,468,075 B2 | 12/2008 | Lang et al. |
| 7,068,867 | B2 | 6/2006 | Adoram et al. | 7,483,743 B2 | 1/2009 | Mann et al. |
| 7,083,614 | B2 | 8/2006 | Fjield et al. | 7,488,231 B2 | 2/2009 | Weston |
| 7,118,852 | B2 | 10/2006 | Purdum | 7,490,085 B2 | 2/2009 | Walker et al. |
| 7,125,676 | B2 | 10/2006 | George, Jr. et al. | 7,494,459 B2 | 2/2009 | Anstadt et al. |
| 7,129,091 | B2 | 10/2006 | Ismagilov et al. | 7,497,119 B2 | 3/2009 | Brooks et al. |
| 7,132,804 | B2 | 11/2006 | Lys et al. | 7,509,869 B2 | 3/2009 | Liu et al. |
| 7,156,863 | B2 | 1/2007 | Sonnenschein et al. | 7,510,536 B2 | 3/2009 | Foley et al. |
| 7,157,233 | B2 | 1/2007 | Fischer et al. | 7,510,838 B2 | 3/2009 | Fischer et al. |
| 7,157,426 | B2 | 1/2007 | Quay et al. | 7,510,873 B2 | 3/2009 | Mistry et al. |
| 7,165,451 | B1 | 1/2007 | Brooks et al. | 7,516,671 B2 | 4/2009 | Liu et al. |
| 7,178,747 | B2 | 2/2007 | Yadav et al. | 7,520,634 B2 | 4/2009 | Ducharme et al. |
| 7,180,252 | B2 | 2/2007 | Lys et al. | 7,524,379 B2 | 4/2009 | Bailey et al. |
| 7,186,691 | B2 | 3/2007 | Quay et al. | 7,525,254 B2 | 4/2009 | Lys et al. |
| 7,186,692 | B2 | 3/2007 | Quay et al. | 7,531,098 B2 | 5/2009 | Robinson et al. |
| 7,187,790 | B2 | 3/2007 | Sabol et al. | 7,539,533 B2 | 5/2009 | Tran |
| 7,187,960 | B2 | 3/2007 | Abreu | 7,539,534 B2 | 5/2009 | Orenstein et al. |
| 7,192,402 | B2 | 3/2007 | Amano et al. | 7,544,662 B2 | 6/2009 | Nelson et al. |
| 7,211,073 | B2 | 5/2007 | Fitzgerald et al. | 7,551,161 B2 | 6/2009 | Mann et al. |
| 7,221,104 | B2 | 5/2007 | Lys et al. | 7,558,622 B2 | 7/2009 | Tran |
| 7,229,966 | B2 | 6/2007 | Quay et al. | 7,559,931 B2 | 7/2009 | Stone |
| 7,231,254 | B2 | 6/2007 | DiLorenzo | 7,572,028 B2 | 8/2009 | Mueller et al. |
| 7,255,457 | B2 | 8/2007 | Ducharme et al. | 7,580,798 B2 | 8/2009 | Brunner et al. |
| 7,269,516 | B2 | 9/2007 | Brunner et al. | 7,590,449 B2 | 9/2009 | Mann et al. |
| 7,279,338 | B2 | 10/2007 | Kim et al. | 7,593,765 B2 | 9/2009 | Rapoport et al. |
| 7,289,836 | B2 | 10/2007 | Colvin, Jr. | 2009/0143805 A1 | 6/2009 | Palmer et al. |
| 7,300,429 | B2 | 11/2007 | Fitzgerald et al. | | | |
| 7,308,296 | B2 | 12/2007 | Lys et al. | | | |
| 7,324,910 | B2 | 1/2008 | Struempler et al. | | | |
| 7,326,201 | B2 | 2/2008 | Fjield et al. | | | |
| 7,329,402 | B2 | 2/2008 | Unger et al. | | | |

FOREIGN PATENT DOCUMENTS

| | | |
|---|---|---|
| GB | 2333709 B2 | 10/1999 |
| WO | WO 98/26739 A1 | 6/1998 |

LOW ENERGY OR MINIMUM DISTURBANCE METHOD FOR MEASURING FREQUENCY RESPONSE FUNCTIONS OF ULTRASONIC SURGICAL DEVICES IN DETERMINING OPTIMUM OPERATING POINT

BACKGROUND

1. Technical Field

The present disclosure relates to an ultrasonic surgical system. More particularly, but not exclusively, it relates to an ultrasonic surgical system able to achieve precise control of a desired operating point.

2. Background of Related Art

Devices which effectively utilize ultrasonic energy for a variety of applications are well-known in a number of diverse arts. A laparoscopic tool where the surgeon may use a scissors-type, a pistol or trigger type grip outside the body to operate a manipulative, gripping or clamping mechanism at a distal end of the tool within the body is useful for use with ultrasonically operated haemostatic cutting tools. Such haemostatic cutting tools are known from British Patent Number 2333709B, International Patent Applications Numbers PCT/GB99/00162 and PCT/GBOO/01580, and U.S. Pat. No. 5,322,055.

Each of the above identified patents and patent applications describes a surgical tool comprising means to generate ultrasonic vibrations and a waveguide, operatively connected at a proximal end to said generating means, and provided at a distal end with cutting and/or coagulating means. Each tool is provided with a jaw to hold tissue to be treated in contact with the ultrasonically vibrating cutting and/or coagulating means.

The Ampulla (Gaussian) profile was published by Kleesattel (as early as 1962), and is employed as a basis for many ultrasonic devices in surgical applications including devices patented and commercialized by Cavitron and Valleylab (patents by Wuchinich, et al., 1977, Stoddard, et al., 2001) for use in ultrasonic aspiration. The Gaussian profile is used in practice to establish and control the resonance and mechanical gain of devices. A resonator, a connecting body and the device act together as a three-body system to provide a mechanical gain, which is defined as the ratio of output stroke amplitude of the radiating tip to the input amplitude of the resonator. The mechanical gain is the result of the strain induced in the materials of which the resonator, the connecting body and the ultrasonic device are composed.

The magnetostrictive transducer coupled with the connecting body functions as the first stage of the booster device with a mechanical gain of about 2:1, due to the reduction in area ratio of the wall of the complex geometry. The major diameter of the device transitions to the large diameter of the Gaussian in a stepped device geometry with a gain of as large as about 5:1, again due to reduction in area ratio. The mechanical gain increases in the Gaussian due to the Square Root of (1+2*Ln (Area Ratio)), where Ln is the natural logarithm, or about 2:1 for the devices of interest. The total mechanical gain is the product of these constituents, or as large as 20:1 for this example. Thus, the application of ultrasonically vibrating surgical devices used to fragment and remove unwanted tissue with significant precision and safety has led to the development of a number of valuable surgical procedures. Accordingly, the use of ultrasonic aspirators for the fragmentation and surgical removal of tissue from a body has become known. Initially, the technique of surgical aspiration was applied for the fragmentation and removal of cataract tissue. Later, such techniques were applied with significant success to neurosurgery and other surgical specialties where the application of ultrasonic technology through a handheld device for selectively removing tissue on a layer-by-layer basis with precise control has proven feasible.

Certain devices known in the art characteristically produce continuous vibrations having substantially constant amplitude at a predetermined frequency (i.e. 20-30 kHz). Certain limitations have emerged in attempts to use such devices in a broad spectrum of surgical procedures. For example, the action of a continuously vibrating tip may not have a desired effect in breaking up certain types of body tissue, bone, etc. Because the ultrasonic frequency is limited by the physical characteristics of the handheld device, only the motion available at the tip provides the needed motion to break up a particular tissue. All interaction with the tissue is at the tip, some being purely mechanical and some being ultrasonic. The devices may have limitations in fragmenting some tissues. The limited focus of such a device may render it ineffective for certain applications due to the vibrations which may be provided by the handheld device. For certain medical procedures, it may be necessary to use multiple hand held devices or it may be necessary to use the same console for powering different handheld devices.

Certain devices known in the art characteristically produce continuous vibrations having a substantially constant amplitude at a frequency of about twenty to about thirty kHz up to about forty to about fifty kHz. The amplitude is inversely proportional to frequency and directly proportional to wavelength because the higher frequency transducers generally have less powerful resonators. For example, U.S. Pat. Nos. 4,063,557, 4,223,676 and 4,425,115 disclose devices suitable for the removal of soft tissue which are particularly adapted for removing highly compliant elastic tissue mixed with blood. Such devices are adapted to be continuously operated when the surgeon wishes to fragment and remove tissue.

A known instrument for the ultrasonic fragmentation of tissue at an operation site and aspiration of the tissue particles and fluid away from the site is the CUSA™ 200 System Ultrasonic Aspirator; see also U.S. Pat. No. 4,827,911, now sold as the CUSA Excel™. When the longitudinally vibrating tip in such an aspirator is brought into contact with tissue, it gently, selectively and precisely fragments and removes the tissue. Depending on the reserve power of the transducer, the CUSA transducer amplitude can be adjusted independently of the frequency. In simple harmonic motion devices, the frequency is independent of amplitude. Advantages of this unique surgical instrument include minimal damage to healthy tissue in a tumor removal procedure, skeletoning of blood vessels, prompt healing of tissue, minimal heating or tearing of margins of surrounding tissue, minimal pulling of healthy tissue, and excellent tactile feedback for selectively controlled tissue fragmentation and removal.

In many surgical procedures where ultrasonic fragmentation instruments are employed, additional instruments are required for tissue cutting and hemostasis at the operation site. For example, hemostasis is needed in desiccation techniques for deep coagulation to dry out large volumes of tissue and also in fulguration techniques for spray coagulation to dry out the surface of tissues.

The apparatus disclosed in U.S. Pat. Nos. 4,931,047 and 5,015,227 provide hemostasis in combination with an ultrasonically vibrating surgical fragmentation instrument and aspirator. The apparatus effectively provide both a coagulation capability and an enhanced ability to fragment and aspirate tissue in a manner which reduces trauma to surrounding tissue.

U.S. Pat. No. 4,750,488 and its two continuation patents, U.S. Pat. Nos. 4,750,901 and 4,922,902, disclose methods and apparatus which utilize a combination of ultrasonic fragmentation, aspiration and cauterization.

In U.S. Pat. No. 5,462,522, there is disclosed, an ultrasonic therapeutic apparatus. The apparatus includes a water supply unit for supplying cooling water to cool the probe; a suction unit for removing waste matter by suction from the organic tissue treated by means of the cooling water and the probe; an ultrasonic output setting section for setting a preset value for an ultrasonic output from the ultrasonic vibrator; a feedwater output setting section for setting a preset value for a feedwater output from the water supply unit; and a feedwater output control section for controlling the feedwater output setting by the feedwater output setting section so that the preset feedwater output value is a value such that the probe is cooled and is not excessively heated.

In U.S. Published Application 2009/0143805 A1, there is disclosed, cutting instruments that utilize ultrasonic waves generate vibrations with an ultrasonic transducer along a longitudinal axis of a cutting blade. By placing a resonant wave along the length of the blade, high-speed longitudinal mechanical movement is produced at the end of the blade. These instruments are advantageous because the mechanical vibrations transmitted to the end of the blade are very effective at cutting organic tissue and, simultaneously, coagulate the tissue using the heat energy produced by the ultrasonic frequencies. Such instruments are particularly well suited for use in minimally invasive procedures, such as endoscopic or laparoscopic procedures, where the blade is passed through a trocar to reach the surgical site.

In an apparatus which fragments, cuts or coagulate tissue by the ultrasonic vibration of a tool tip, it is desirable, for optimum efficiency and energy utilization, that the transducer which provides the ultrasonic vibration operate at resonant frequency. The transducer design establishes the resonant frequency of the system, while the generator tracks the resonant frequency. The generator produces the electrical driving signal to vibrate the transducer at resonant frequency. However, changes in operational parameters, such as, changes in temperature, thermal expansion and load impedance, result in deviations in the resonant frequency.

More specifically, as the temperature increases, the material density decreases and the speed of sound increases. The increase in temperature may lead to a lower equivalent mass of the key system components, especially the device which has a very low mass and can heat up and cool down quickly. The lower equivalent mass may lead to a change in equivalent resonant frequency. Additionally, when the water supply unit supplies water to cool down the device, the water adds mass to the device as well as acting as a coolant to maintain the temperature of the device. As such, the presence of water may change the equivalent resonant frequency.

SUMMARY

The present disclosure relates to an ultrasonic system that includes an ultrasonic device configured to impart ultrasonic energy to tissue. The system also includes an ultrasonic generator configured to supply power to the ultrasonic device. The ultrasonic generator has a controllable drive signal generator as part of a negative feedback loop configured to provide a drive signal, a controllable noise signal generator configure to provide a noise signal, and a controller. The controller receives an output signal from the ultrasonic device and the noise signal from the noise signal generator, calculates a transfer function estimate based on the output signal and the noise signal, and adjusts the drive signal generator based on the calculated transfer function estimate.

In another embodiment according to the present disclosure, an ultrasonic generator configured to supply power to an ultrasonic device is provided. The ultrasonic generator has a drive signal generator configured to provide a drive signal, a noise signal generator configured to provide a noise signal, and an adder configured to combine the drive signal and the noise signal. The ultrasonic generator also includes an amplifier having a gain configured to amplify the combined signal. A controller is configured to receive an output signal from the ultrasonic device and the noise signal from the noise signal generator, calculate a transfer function estimate based on the output signal, the noise signal and the gain, and adjust the drive signal generator based on the calculated transfer function estimate.

In yet another embodiment according to the present disclosure, an ultrasonic generator configured to supply power to an ultrasonic device is provided. The ultrasonic generator has a drive signal generator configured to provide a drive signal, an amplifier having a gain configured to amplify the drive signal, a noise signal generator configured to provide a noise signal, and a resonance circuit configured to provide an output to the resonator of the ultrasonic device. The ultrasonic generator also includes a transformer having a first primary winding coupled to the amplifier, a second primary winding coupled to the noise signal generator and a secondary winding coupled to the resonance circuit. A controller is also provided that is configured to receive an output signal from the ultrasonic device and the noise signal from the noise signal generator, calculate a transfer function estimate based on the output signal and the noise signal, and adjust the drive signal generator based on the calculated transfer function estimate.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
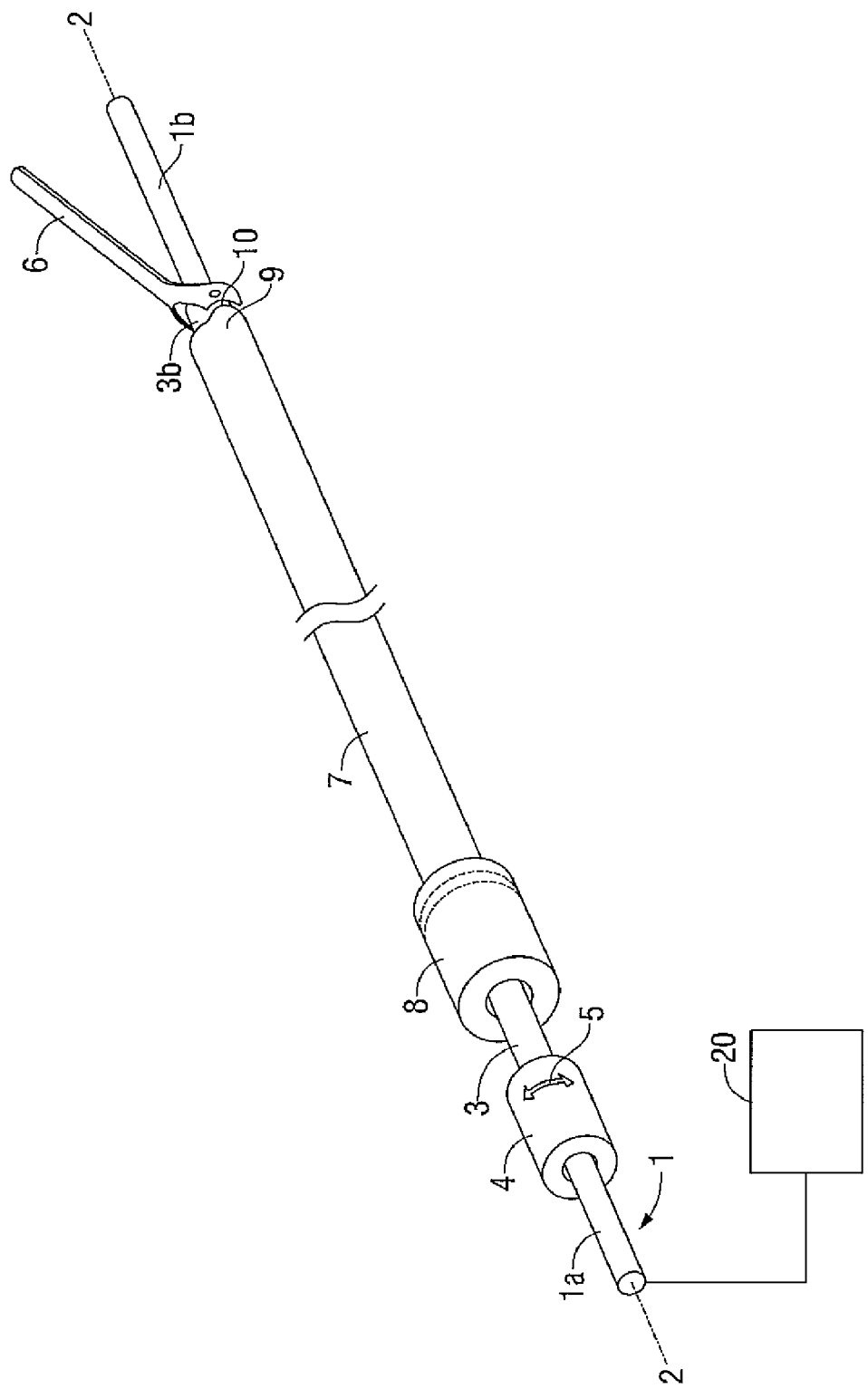
FIG. 1 is a perspective view of an ultrasonic device in accordance with an embodiment of the present disclosure.

Particular embodiments of the present disclosure will be described hereinbelow with reference to the accompanying drawings; however, it is to be understood that the disclosed embodiments are merely exemplary of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Embodiments of the presently disclosed ultrasonic surgical system are described in detail with reference to the drawings, in which like reference numerals designate identical or corresponding elements in each of the several views. As used herein, the term "distal" refers to that portion of the instrument, or component thereof which is further from the user while the term "proximal" refers to that portion of the instrument or component thereof which is closer to the user.

Referring now to the drawings and to FIG. 1 in particular, a surgical tool, in this case an ultrasonic surgical haemostatic tool, comprises an elongate waveguide 1 for ultrasonic vibrations (torsional mode ultrasonic vibrations are preferred, although longitudinal mode ultrasonic vibrations may also be utilized). An example of such an ultrasonic surgical device is disclosed in U.S. Pat. No. 7,520,865 to Young et al. currently owned by and assigned to Covidien AG, the entire contents of which are incorporated herein by reference. The waveguide 1 defines a longitudinal axis of the tool, as shown by dotted line 2-2. A proximal end 1a of the waveguide 1 is mounted to an ultrasonic vibration generator 20 which will be described in more detail hereinbelow.

The waveguide 1 is disposed coaxially within an elongate carrier tube 3, which is mounted at its proximal end to a cylindrical turning element 4. The carrier tube 3 and the turning element 4 are rotatable as a unit about the longitudinal axis 2, in the sense of arrows 5. The turning element 4 is acted on by a trigger mechanism or other manual operating means, as detailed below. A jaw member 6 is mounted pivotably to a distal end 3b of the carrier tube 3.

A plurality of spacers (not shown) may be provided between the waveguide 1 and an inner wall of the carrier tube 3, insulating the carrier tube 3 from ultrasonic vibrations transmitted by the waveguide 1 and maintaining their relative disposition.

An outer tube 7 is disposed coaxially around the carrier tube 3 and the waveguide 1. The outer tube 7 is mounted at its proximal end to a mounting block 8, which is mounted non-rotatably to a handset of the tool (not shown in this Figure). At its distal end, the outer tube 7 is provided with a guide lobe 9, which bears on a rearward facing contact surface 10 of the jaw member 6. The turning element 4 and the mounting block 8 are biased apart, for example with a spring, other resilient device, or cam means such that the guide lobe 9 and the contact surface 10 remain co-operatingly in contact one with another.

When the carrier tube 3 is rotated, the contact surface 10 of the jaw member 6 mounted thereto moves across the guide lobe 9 of the stationary outer tube 7, thereby causing a pivoting movement of the jaw member 6 away from or towards contact with the distal end 16 of the waveguide 1, as detailed below.

The outer tube 7 also acts as a protective sheath for the greater part of the rotatable carrier tube 3 and the waveguide 1, for example protecting them from body fluids as far as possible. In a preferred embodiment of the tool, the carrier tube 3 and the outer tube 7 are detachable from the handset of the tool. The carrier tube 3 and the jaw member 6 that it carries may then be withdrawn in a distal direction from the outer tube 7, so that each may be cleaned and sterilized separately before re-use, or alternatively so that either or both may be disposed of and replaced with a fresh equivalent.

Figure 2:
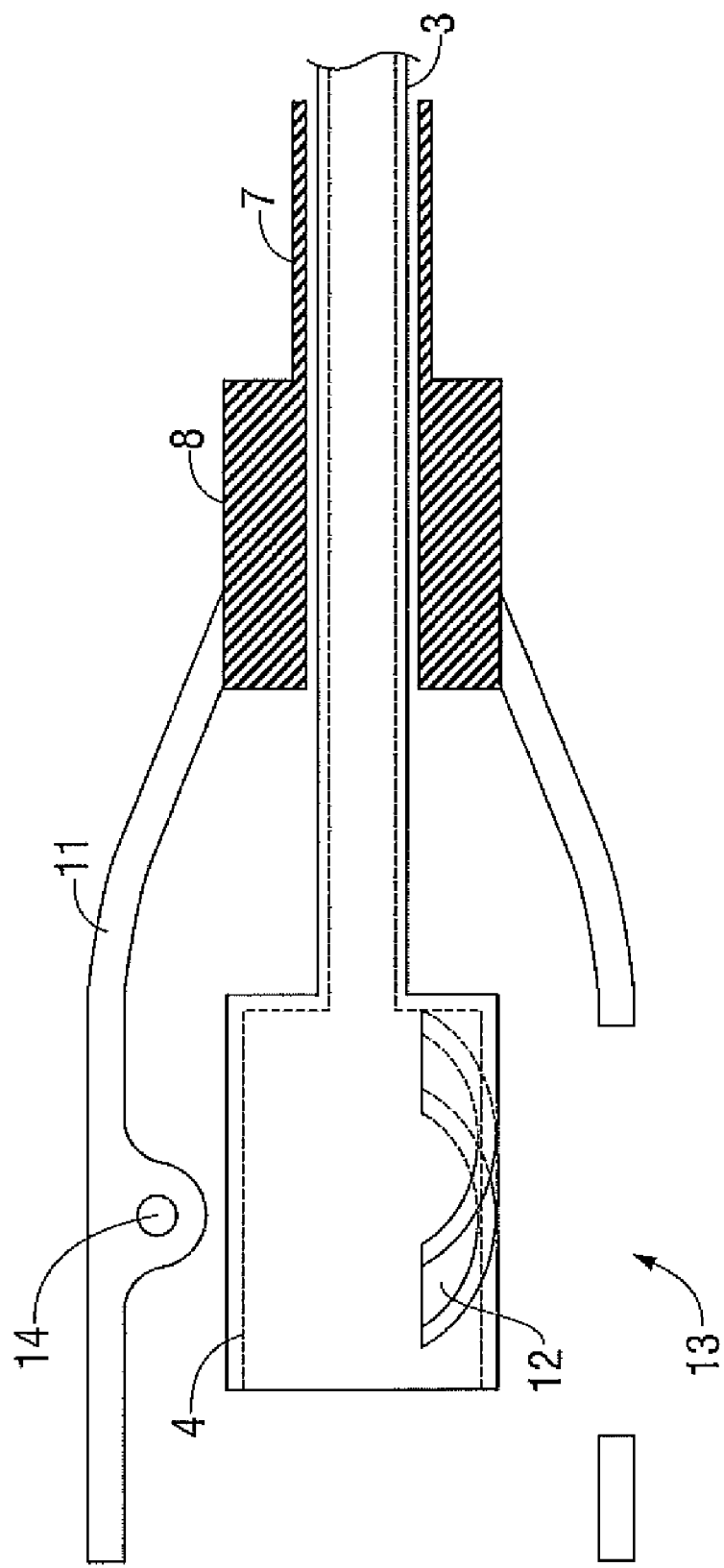
FIG. 2 is a cross-sectional view of a part of the handset of the tool of FIG. 1 including a turning element.

FIG. 2 shows a part of the handset of the tool, together with proximal portions of the outer tube 7 and the carrier tube 3. The mounting block 8 is mounted, permanently or removably, to a handset casing 11. In this particular embodiment of the tool, the turning element 4 is provided with a part helical slot 12 in its cylindrical wall, which is adapted to receive a driving stud (not shown) mounted to a trigger mechanism (not shown) which extends out of the casing 11 through an aperture 13 provided therefor. The trigger mechanism may optionally be mounted to a pivot mounting 14 on the casing 11, as shown, or to a pivot mounting disposed adjacent the aperture 13. Pivoting movement of the trigger mechanism, which is configured to be grasped by a hand of a user, moves the driving stud in a generally longitudinal direction. As the driving stud is constrained to move within the part helical slot 12, a forward motion of the stud causes the turning element 4, and hence the carrier tube 3, to rotate in an anticlockwise sense (viewed from a proximal end of the tool) and a rearward motion of the stud causes the turning element 4 and the carrier tube 3 to rotate in a clockwise sense.

The ultrasonic vibration generator is conveniently mounted inside a detachable element of the casing 11. FIG. 2 shows the handset with that element detached, and the waveguide 1, mounted to the ultrasonic generator, thereby withdrawn from its operating disposition disposed coaxially within the carrier tube 3.

Figure 3:
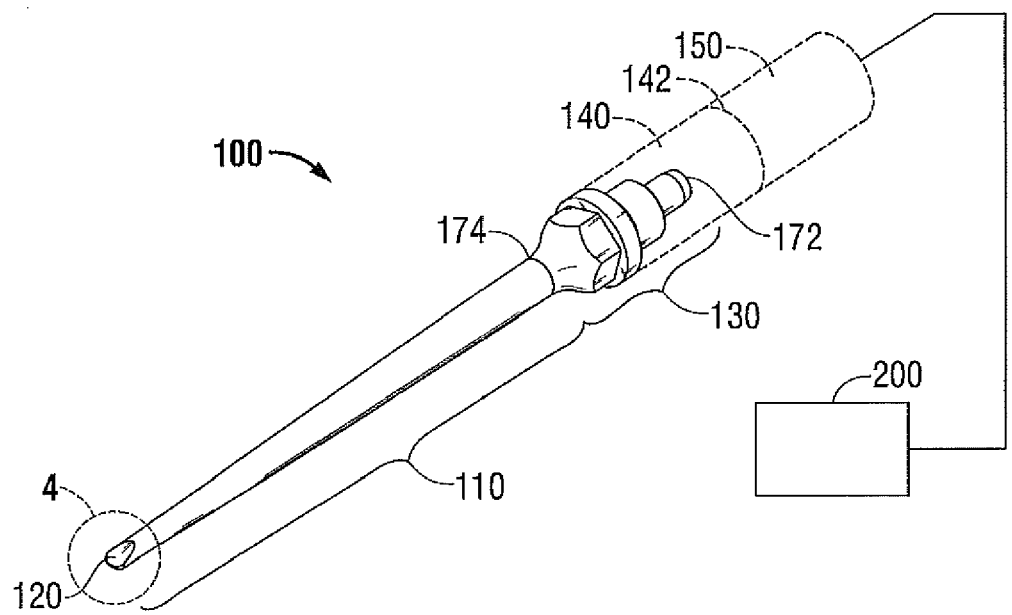
FIG. 3 is a perspective view of an ultrasonic device in accordance with an embodiment of the present disclosure.

An ultrasonic device 100, in accordance with one embodiment of the present disclosure, is illustrated in FIG. 3. Ultrasonic device 100 is adapted for use in an ultrasonic surgical system having an ultrasonic handpiece. An example of such an ultrasonic surgical system is disclosed in U.S. Pat. No. 6,214,017 to Stoddard et al. currently owned by and assigned to Sherwood Services AG, the entire contents of which are incorporated herein by reference. Alternatively, ultrasonic device 100 may be adapted for use with the ultrasonic surgical system disclosed in U.S. Pat. No. 4,063,557 to Wuchinich et al., the entire contents of which are incorporated herein by reference.

Figure 4:
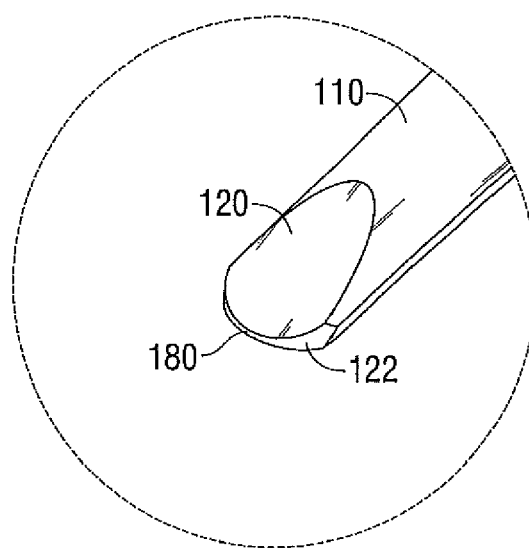
FIG. 4 is an enlarged view of a tip of the ultrasonic device of FIG. 3.

Referring to FIGS. 3 and 4, in one embodiment of the present disclosure, ultrasonic device 100 includes an adapter 130 having a first or proximal end 172 and a second or distal end 174. Extending from proximal end 172, adapter 130 includes a fillet 132, a nut 134 and a flange 136 terminating at distal end 174. Flange 136 includes a leading edge 138. Proximal end 172 of adapter 130 is configured to connect ultrasonic device 100 to an ultrasonic handpiece or resonator 150 via a connecting portion 140. Connecting portion 140 is capable of coupling ultrasonic device 100 and connecting portion 140 to ultrasonic handpiece or resonator 150. As used herein, the term "resonator" is used to refer to what is often referred to in the literature as an ultrasonic handpiece. Ultrasonic device 100 includes an elongated member 110 having a first or proximal end which coincides with distal end 174 of adapter 130. Elongated member 110 has a second or distal end 180, and distal end 174 of adapter 130 is joined, in one embodiment unitarily, to the coinciding proximal end of elongated member 110. Distal end 180 of elongated member 110 is configured as a tip lead 120. Tip lead 120 extends from a first or proximal end, as is discussed in more detail below.

Connecting portion 140 includes a first or proximal end 142 which is configured to connect to a resonator 150 at a distal end thereof. Resonator 150 includes, in one embodiment, a magnetostrictive transducer, although other transducer types can be included such as a piezoelectric transducer. Resonator 150 is supplied power from ultrasonic generator 200 (described in more detail below) such that resonator 150 operates at a desired frequency. In one embodiment, ultrasonic device 100 is made of titanium, although other materials such as stainless steel can be used.

Figure 5:
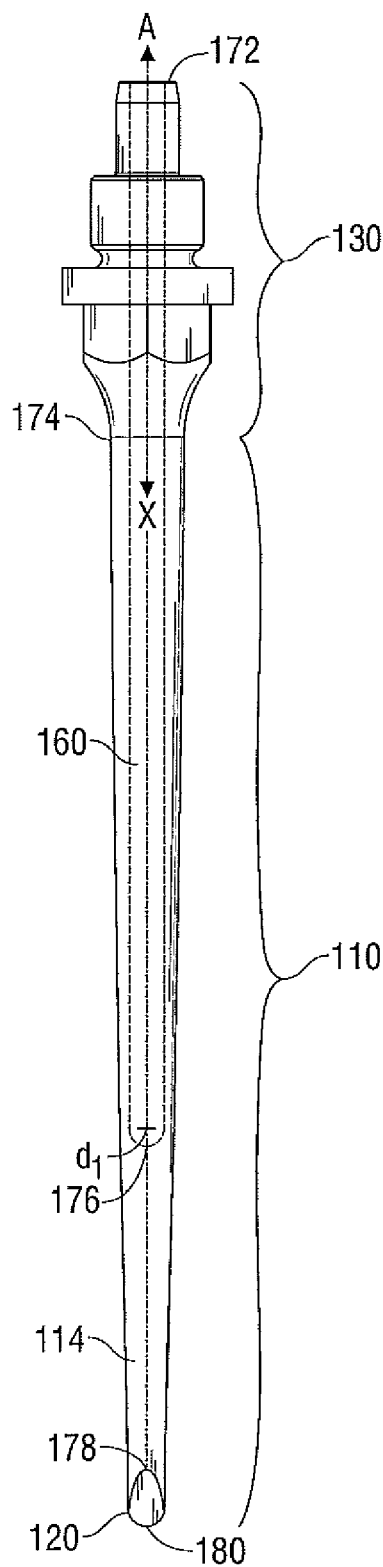
FIG. 5 is a top view of the ultrasonic device of FIG. 3 with a channel shown in phantom.

As seen in FIG. 5, an internal channel 160 is formed within elongated member 110. As is known in the art, the channel terminates in the connecting body, and does not continue in the resonator. The resonator is typically a laminated core-stack of Permanickel. In most implementations, the central channel supports aspiration suction of tissue. The channel also affords greater mechanical gain because the gain is dependent on the reduction in area ratio of the thin walls. The primary purpose of the channel is to support gain for bone tips with the chisel/awl distal ends. The internal channels of the bone abrading tips in the disclosure shown and described below would also aid in cooling, where irrigation liquid is suctioned via the internal diameter channel. Surgical procedures on bone typically employ an auxiliary suction tube to remove the larger volumes of irrigation liquid and bone debris.

Figure 6:
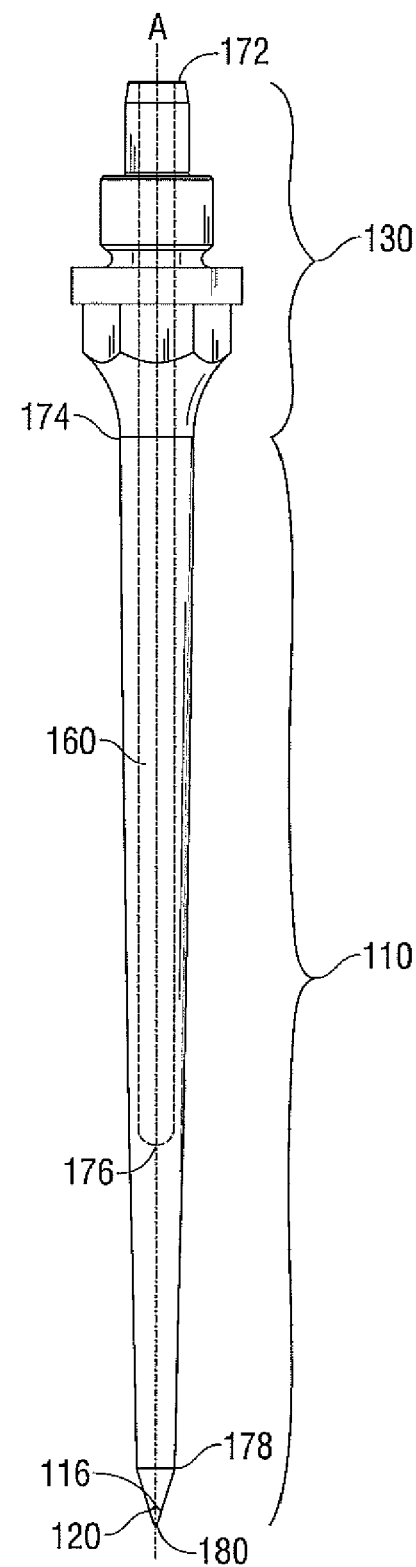
FIG. 6 is a side view of the ultrasonic device of FIG. 3.
Figure 7:
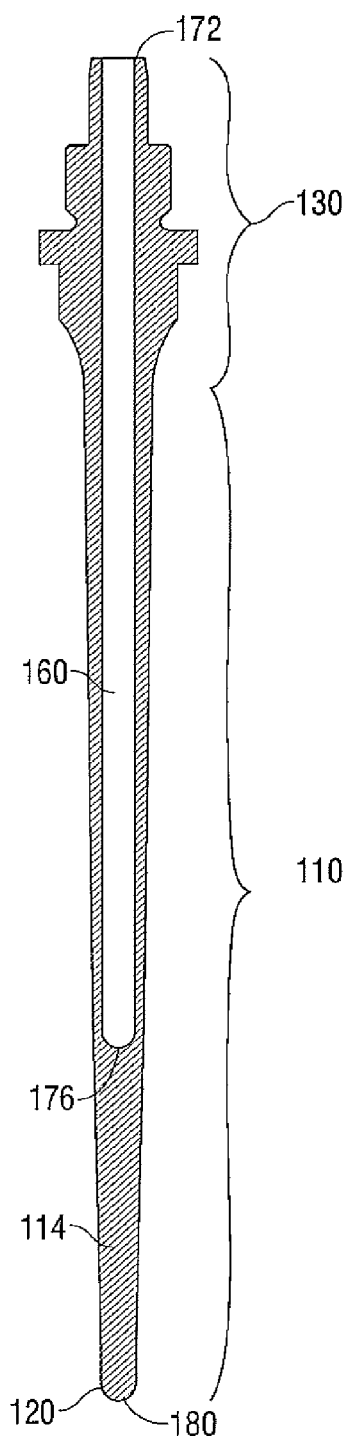
FIG. 7 is a cross-sectional view of the ultrasonic surgical device of FIG. 5.
Figure 8:
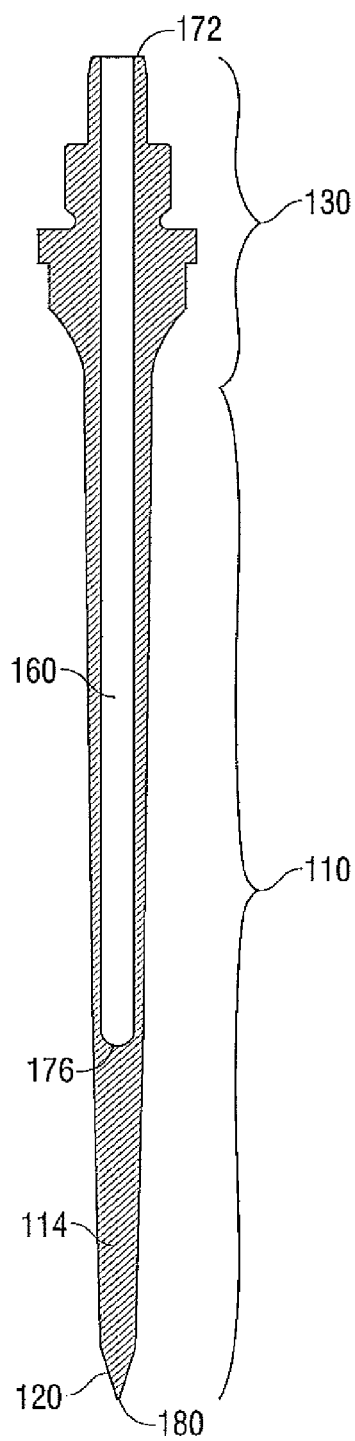
FIG. 8 is a cross-sectional view of the ultrasonic surgical device of FIG. 6.

Referring to FIGS. 5-6, FIG. 8 is a top view of ultrasonic device 100 of FIG. 3 with channel 160 shown in phantom formed within elongated member 110. FIG. 6 is a side view of ultrasonic device 100 of FIG. 3 with channel 160 in phantom formed within elongated member 110. FIG. 7 is a cross-sectional view of ultrasonic surgical device 100 of FIG. 5 showing channel 160 formed within elongated member 110. FIG. 8 is a cross-sectional view of ultrasonic surgical device 100 of FIG. 6 again showing channel 160 formed within elongated member 110. Internal channel 160 is formed within adapter 130 and elongated member 110 of ultrasonic device 100.

Elongated member 110 is tapered such that the cross-sectional area is a maximum at proximal end 174 interfacing with adapter 130 and is a minimum at proximal end 178 of tip lead 120. Channel 160 is a substantially constant diameter central hole of diameter $d_1$ formed within elongated member 110 to enable enhanced mechanical gain in device 100. In the case of a device with a channel, it is the area ratio of the cross-sectional area based on the outer diameter of the elongated member 110 near the leading edge 138 of flange 136 versus the cross-sectional area based on the outer diameter of the elongated member 110 at the distal end 176. The area ratio along the length L of the device is decreased towards tip lead 120 at the distal end of elongated member 110, and velocity and elongation of the titanium particles are increased. The ultrasonic wave is supported by particle motion in the titanium. The particles vibrate about their neutral position in a longitudinal or extensional wave. The particles do not move along the length of the device, but only vibrate, just as a cork or bobber shows that a wave passes through water via the liquid. As the device wall thickness decreases, more strain occurs in the metal as the particles move a greater distance about their neutral position. The displacement of the end of the device is due to strain along the device. All the particles supporting the wave are moving at the same resonant frequency. The greater the strain, the greater the velocity of the particles necessary to maintain the same frequency.

As best illustrated in FIG. 4, distal end 180 of tip lead 120 has a semi-circular planar surface configuration 122, such that distal end 180 of ultrasonic device 100 is in the form of a chisel and an awl. (Awls are utilized in manual boring of holes, such as in boring leather or wood). Tip 180 of ultrasonic device 100 is blunt or dull. The boring of holes with device 100 is better facilitated with slightly semi-circular manual motion; however plunge cuts in bone and wood have been accomplished with just longitudinal motion of device 100. The combination of the chisel and awl distal end 180 of device 100 supports defined cutting or abrasion of sections, planes, notches, grooves, and holes in bone. Channel or central hole 160 extends from proximal end 172 of adapter 130 to approximately distal end 176 which coincides with proximal end of solid portion 114 of elongated member 110.

Figure 9:
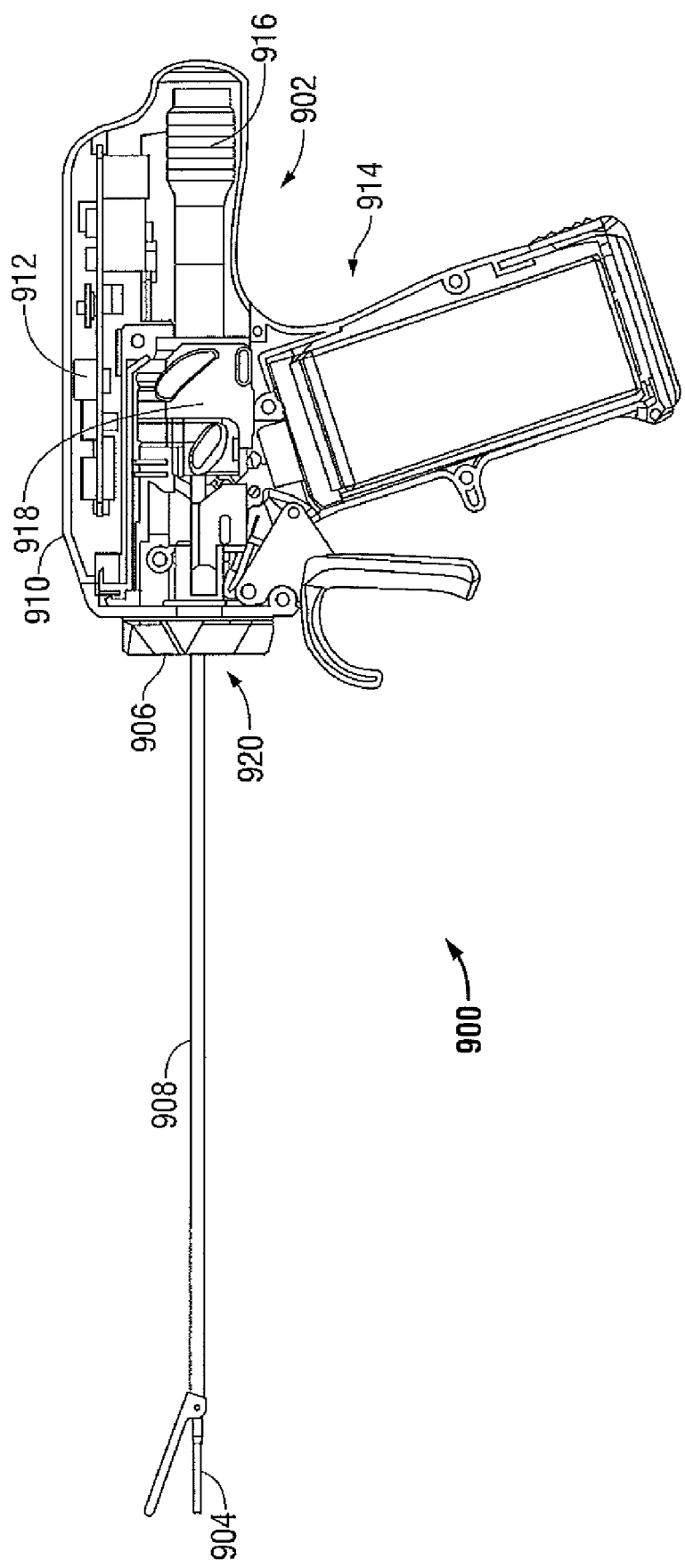
FIG. 9 is a side elevational view of an exemplary handle with the left-side shell removed in accordance with an embodiment of the present disclosure.

Another example of an ultrasonic surgical device is disclosed in United States Published Application Number 20090143805 to Palmer et al. currently owned by and assigned to Syntheon, LLC, the entire contents of which are incorporated herein by reference. Referring now to FIG. 9, an ultrasonic surgical device 900 in accordance with an embodiment of the present disclosure is depicted. When an ultrasonic-movement-generation assembly 902 is coupled to a handle 914, the transducer 916 is caused to be releasably physically coupled to a waveguide 904, 908 through the transducer attachment port 918 and waveguide attachment port 920. It is envisioned that the transducer assembly 916 can be temporarily locked into a fixed rotational position so that the waveguide 904 can be attached to the threads (not shown) with sufficient force. This physical coupling between the waveguide 904 and the transducer assembly 916 allows the transducer assembly 916 to impart movement to the waveguide 904 when power is applied to the transducer assembly 916.

The device 900 has a spindle 906 that attaches to the waveguide 908. The spindle 906 has indentions that allow a surgeon to easily rotate the spindle 906 and, therefore, the attached waveguide 908 and transducer assembly 916 that is attached to the waveguide 908. Such a configuration is useful for obtaining the proper cutting-blade angle during surgery. To provide for this rotation, in one embodiment, the transducer assembly 916 is able to rotate freely within the transducer housing 910.

During initial coupling of the transducer assembly 916 and waveguide 904, all that is needed is that one of the transducer assembly 916 and the waveguide 904 remains relatively stationary with respect to the other. According to one embodiment of the present disclosure, when the transducer assembly 916 is located inside the housing 910 where it cannot be readily secured by the operator, for example, by holding it steady by hand when the waveguide 908 is being secured— the ultrasonic-movement-generation assembly 902 is provided with a button (not shown) that slides into a recess in the housing 910 or, alternatively, by fixing the rotation of the transducer assembly 916 at a maximum rotational angle so that, once the maximum rotation is reached, for example, 360 degrees of rotation, no additional rotation is possible and the waveguide 904 can be screwed thereon. A maximum rotation in the opposite direction will allow the waveguide 904 to be removed as well.

Figure 10:
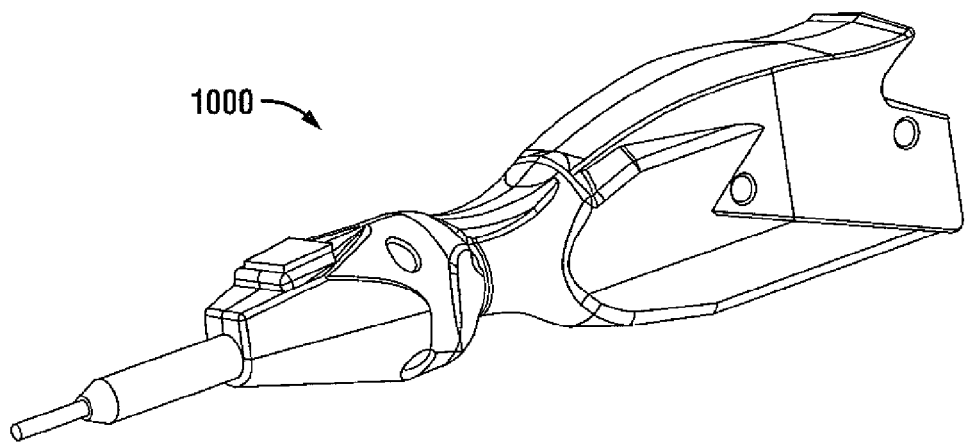
FIG. 10 is a perspective view from the front left side of a hand-held ultrasonic cutting pen device in accordance with an embodiment of the present disclosure.
Figure 11:
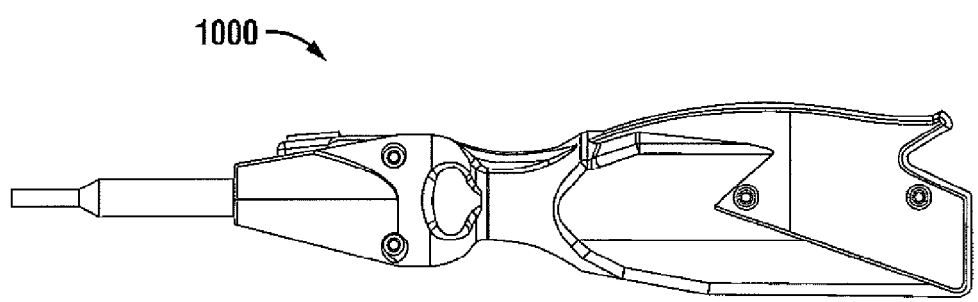
FIG. 11 is a side elevational view of the hand-held ultrasonic cutting pen device of FIG. 10 from the left side.
Figure 12:
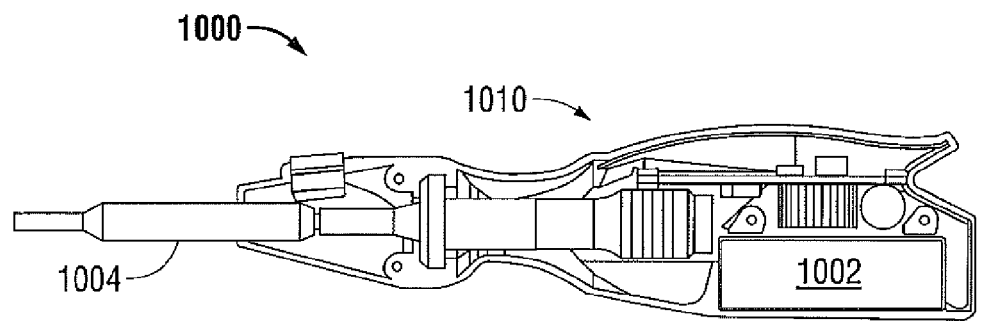
FIG. 12 is a side elevational view of the hand-held ultrasonic cutting pen device of FIG. 11 with the left-side shell removed.

In an alternative exemplary embodiment to the gun device, FIGS. 10 to 12 illustrate an entirely hand-held and fully self-contained cautery and cutting device 1000. This cutting device 1000 reduces the size of the power supply 1002 considerably. Here, in comparison to the previous embodiments, the waveguide 1004 is reduced in length. The ultrasonic generator and the power supply 1002 reside at the handpiece 1010. As in the other embodiments described above, the pen shaped device shown in FIGS. 10 to 12 could have, in accordance with one embodiment, a sealed body 1002, where the body 1002 housing the ultrasonic generator and the power supply 1002 is autoclavable and the waveguide 1004 is simply replaced for each procedure.

Figure 13:
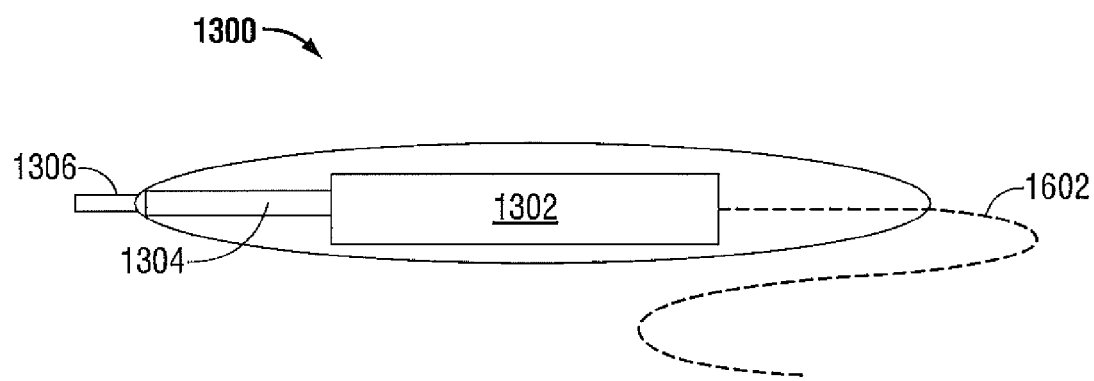
FIG. 13 is a diagrammatic illustration of a hand-held ultrasonic cutting pen device to be connected to a man-portable, control and power supply assembly in accordance with an embodiment of the present disclosure.
Figure 14:
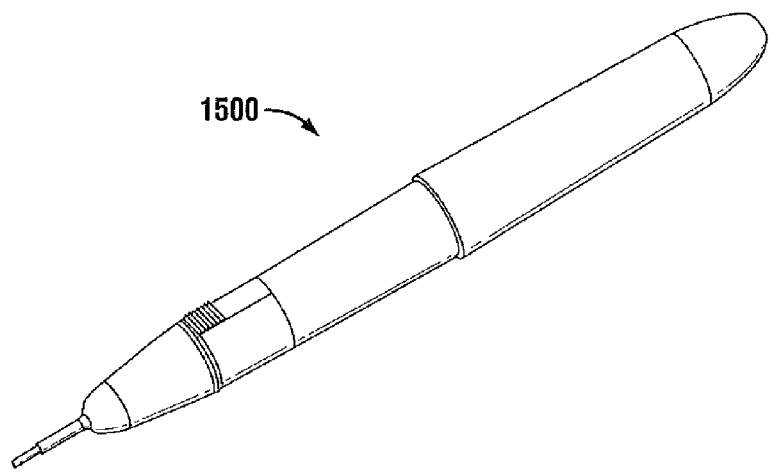
FIG. 14 is a perspective view of a hand-held ultrasonic cutting pen device to be connected to a man-portable, control and power supply assembly in accordance with an embodiment of the present disclosure.
Figure 15:
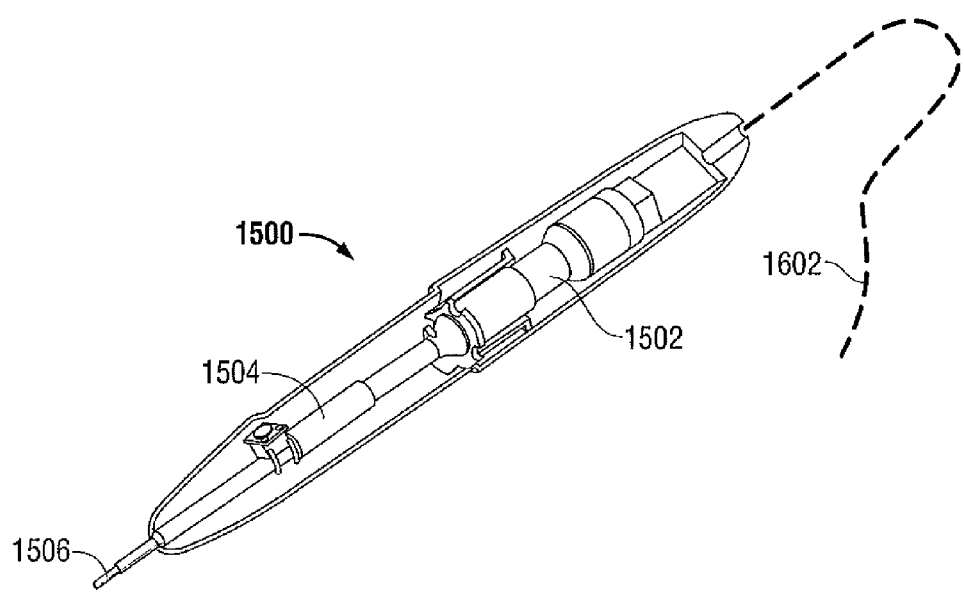
FIG. 15 is a perspective view of the hand-held ultrasonic cutting pen device of FIG. 15 with a left-half shell removed.

FIG. 13 depicts another shape for the cautery/cutting device 1300 that is shaped to fit into a surgeon's hand for ease of use. Another shape for the pen device 1500 is shown in FIGS. 14 and 15 and is similar to a writing pen so that the surgery can be carried out with the device 1500 to approximate writing—a process that is comfortable to most physicians. The pen 1300, 1500 includes all of the transducer components—the transducer 1302, 1502, the protective cannula 1304, 1504, and the waveguide 1306, 1506.

Figure 16:
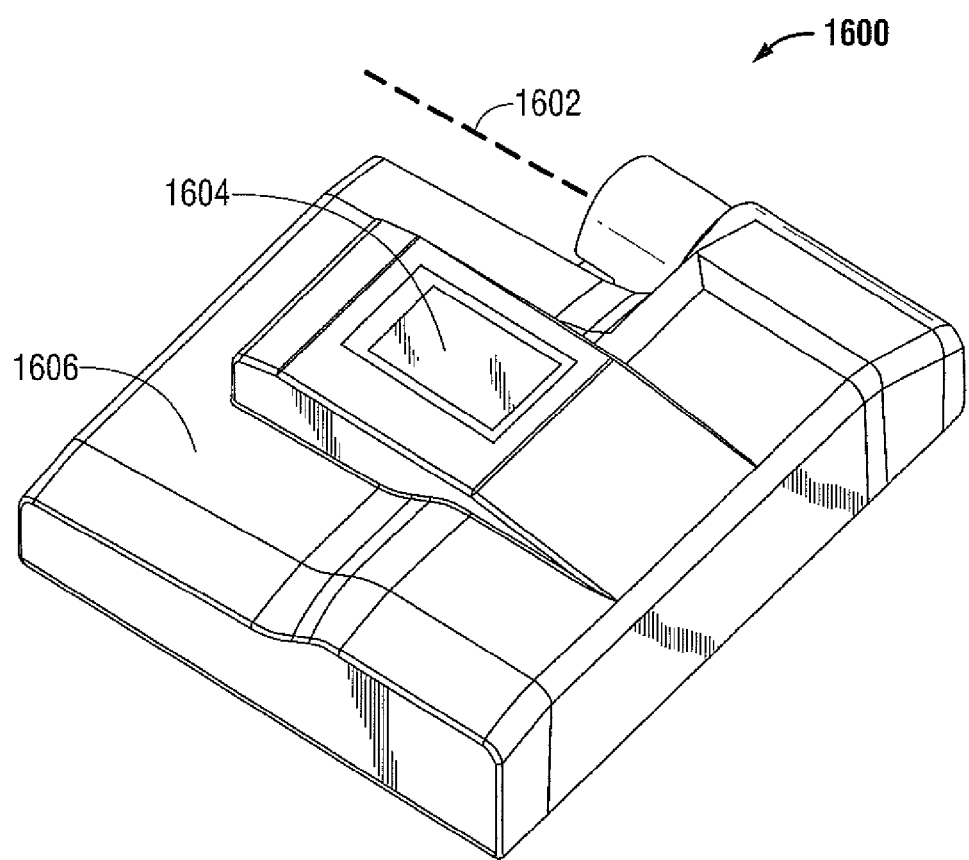
FIG. 16 is a perspective view of a portable, control and power supply assembly to be connected to a hand-held ultrasonic cutting pen device in accordance with an embodiment of the present disclosure.

In these embodiments, the base 1600, shown in FIG. 16, has a body 1606 that houses a self-contained power source (i.e., a battery) and a generator circuit operable to generate an output waveform and is sized to be handheld. The base 1600 is connected through a communications and power tether cord 1602, illustrated diagrammatically in the figures with a dashed line, to the pen-shaped ultrasonic waveguide handle 1500, shown in FIGS. 15-16. When in operation, the transducer 1502 within the handle 1500 is driven by a plurality of driving waves output from the waveform generator within the body 1506.

The base 1600 has a user interface 1604 that can be used to communicate data and carry out functions of the device, such as testing and operation. Through the user interface 1604, the device can be tested in the sealed package without even opening the package. For instance, in one embodiment, a user can press one or more non-illustrated buttons (physical or electronic) in a given sequence (e.g., 5 times in a row) and, thereby, cause the user interface 1604 to display a status of the battery and/or a status of the logic circuitry, all without having to remove it from the sealed package. This is helpful in case of a defect, such as a bad battery, as the purchaser would be able to return the device to the manufacturer before use and, thereby, prove non-use of the device to receive credit. In this embodiment, all of the ultrasonic generator components reside in the base 1600.

The base 1600 is also provided with a non-illustrated clothing attachment mechanism that can be a simple belt clip, or any other way of attaching a device to a wearer. The clothing attachment mechanism allows a surgeon or nurse to wear the base 1600 during a surgery so that the cord 1602 will always be of sufficient length, i.e., as long as his arm can reach, no matter where the surgeon is standing.

Figure 17:
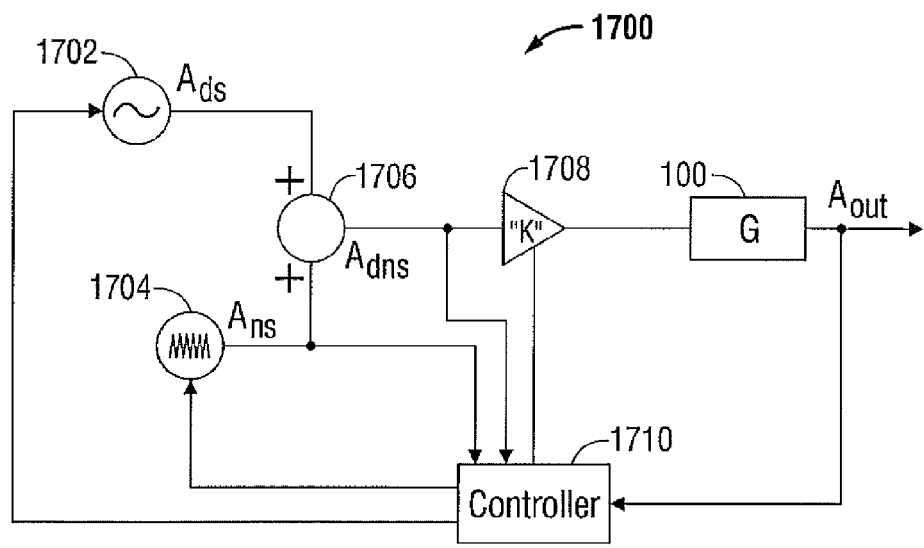
FIG. 17 is a schematic of an ultrasonic generator in accordance with an embodiment of the present disclosure.

Referring to FIG. 17, an apparatus or ultrasonic generator 1700 is provided which is configured to supply power to the resonator 150. Ultrasonic generator 1700 uses a negative feedback loop to control the output of the ultrasonic generator 1700. Ultrasonic generator 1700 includes a controllable drive signal generator 1702 that generates a drive signal ($A_{ds}$) to control the ultrasonic device. The drive signal generator 1702 outputs a sine wave in an embodiment of the present disclosure. The sine wave may also be substituted with a square wave, triangular wave or a pulse width modulated (PWM) form of the sine wave. Noise generator 1704 is also provided which outputs a controllable noise signal ($A_{ns}$). The ultrasonic device tends to self heat which would increase resonance. Alternatively, the added load at the distal tip of the device will add mass and/or compliance, which will also change the resonance. The resonance changes quickly as the ultrasonic device cools again or is transiently loaded and unloaded. By adding a noise signal such as a "pink" noise or narrowband white noise, with many Fast Fourier Transform (FFT) bins averaged together, an operating point can be determined and the ultrasonic device could be tuned to the operating point. A FFT is an efficient algorithm to compute the discrete Fourier transform (DFT) and its inverse. A DFT decomposes a sequence of values into components of different frequencies. This operation is useful in many fields but computing it directly from the definition is often too slow to be practical. An FFT is a way to compute the same result more quickly: computing a DFT of N points in the obvious way, using the definition, takes $O(N^2)$ arithmetical operations, while an FFT can compute the same result in only $O(N \log N)$ operations. The difference in speed can be substantial, especially for long data sets where N may be in the thousands or millions—in practice, the computation time can be reduced by several orders of magnitude in such cases, and the improvement is roughly proportional to N/log(N).

In another embodiment of the present disclosure, a pseudo random noise sequence (PRNS) may be provided as a noise signal by noise signal generator 1704. Using a PRNS noise signal allows the ultrasonic system to determine the phase of an output signal with respect to the input signal.

The drive signal and noise signal are combined ($A_{dns}$) by adder 1706 and the combined signal is provided to amplifier 1708. Amplifier 1708 has a gain "k" which can be a predetermined value set by the manufacturer or could be adjusted by a user of the ultrasonic system. The output of amplifier 1708 is provided to the ultrasonic device 100 as described above. Ultrasonic device has a transfer function "G" that determines the resonance and electro-mechanical gain of the device as described above. Ultrasonic device outputs an ultrasonic signal ($A_{out}$) proportional to the stroke or mechanical force produced by the ultrasonic device that is to be controlled by the negative feedback loop.

As shown in FIG. 17, the ultrasonic signal is provided to a controller 1710. Controller 1710 also receives or has a priori information on the statistics of the noise signal from noise signal generator 1704, the drive signal from drive signal generator 1702, and the gain "k" from amplifier 1708. Controller 1710 may be any available processor or logic circuit configured to perform the functions described below. Controller 1710 may also include a memory configured to store predetermined or measured parameters to use in the controller's 1710 operations. Although not shown, controller 1710 may be coupled to an input device, such as a keypad, keyboard, mouse, touch screen, scanner, or the like. Controller 1710 may also be coupled to an output device such as any type of display that provides a visual indication such as a monitor, light emitting diode display, liquid crystal display, printer, or the like.

Because the increase in temperature may lead to a lower equivalent mass of the key ultrasonic system components (for instance, in one embodiment, the water supply unit supplies water to cool down the device where the water adds mass to the device as well as acting as a coolant to maintain the temperature of the device), the equivalent resonant frequency of the ultrasonic device may change. Accordingly, controller 1710 applies a transfer function using the FFT's of the ultrasonic signal output and the noise signal from noise signal generator 1704. More specifically, the controller 1710 calculates the new transfer function estimate "Ĝ" of the ultrasonic device by dividing the average of the output power FFT's $|A_{out}|^2$ by the input FFT's noise power $|A_{ns}|^2$ and gain "k". The controller 1710 can also determine the phase difference between the output power signal and the combined signal by time aligning the noise signal from noise signal generator 1704 and the noise signal in the output power signal. The phase difference may also be determined using a phase-locked loop (PLL) circuit (not shown). Based on the new transfer function estimate "Ĝ", a new equivalent resonance frequency can be determined. Drive signal generator 1702 is adjusted by the controller 1710 to provide a new drive signal based on the new equivalent resonance frequency.

Figure 18:
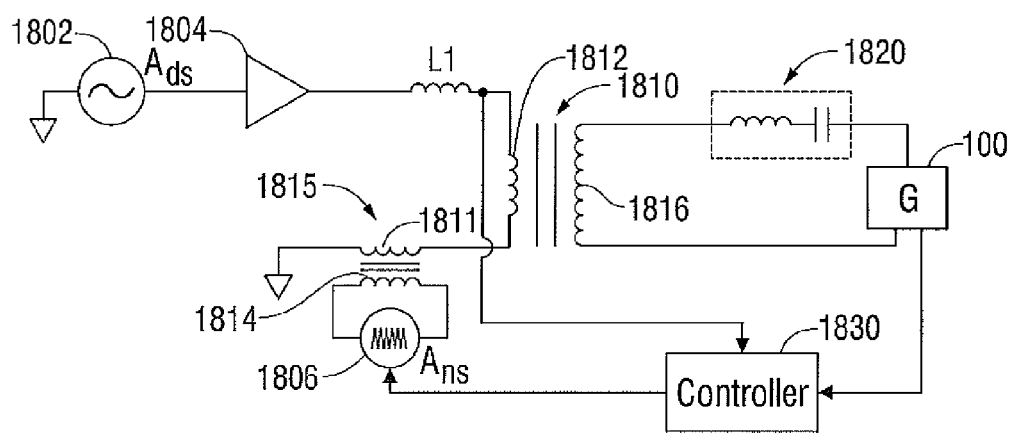
FIG. 18 is a schematic of an ultrasonic generator in accordance with an embodiment of the present disclosure.

FIG. 18 depicts another embodiment of an ultrasonic generator 1800 in accordance with the present disclosure. As shown in FIG. 18, a drive signal generator 1802 provides a drive signal to amplifier 1804. Amplifier 1804 may be a non-linear amplifier such as Class D amplifier. A Class D amplifier is an electronic amplifier which, in contrast to the active resistance used in linear mode AB-class amplifiers, uses the switching mode of transistors to regulate power delivery. The amplifier, therefore, features high power efficiency (low energy losses), which additionally results in lower weight by eliminating bulky heat sinks. Additionally, if voltage conversion is necessary, the on-the-way high switching frequency allows the bulky audio transformers to be replaced by small inductors. Low pass LC-filtering smoothes the pulses out and restores the signal shape on the load.

The output of amplifier 1804 is provided to an inductor L1 which is coupled to a primary winding 1812 of a transformer 1810. Unlike the embodiment described in FIG. 17, the ultrasonic generator 1800 provides a noise signal generator 1806 after the amplifier 1804. The noise source is coupled to a winding on the primary side 1814 of transformer 1815. The secondary winding of 1811 of transformer 1815 is coupled to primary winding 1812 of transformer 1810. The secondary winding 1816 of transformer 1810 is coupled to an LC circuit or resonance circuit 1820 which then provides an output of both the drive signal and the noise signal to a resonator such as resonator 150 of ultrasonic device 100 described hereinabove. An LC circuit is a resonant circuit or tuned circuit that consists of an inductor, represented by the letter L, and a capacitor, represented by the letter C. When connected together, an electric current can alternate between them at the circuit's resonant frequency. The LC circuit is typically used to compensate for losses in the class D amplifier that may occur due to complex loading effects of the ultrasonic device.

Similar to ultrasonic generator 1700, the output of the ultrasonic device is provided to a controller 1830 which calculates the new transfer function estimate "Ĝ" of the ultrasonic device by dividing the average of the output power FFT's $|A_{out}|^2$ by the input FFT's noise power $|A_{ns}|^2$. The controller 1830 can also determine the phase difference between the output power signal and the combined signal by "time aligning" the noise signal from noise signal generator 1806 and the noise signal in the output power signal. Based on the new transfer function estimate "Ĝ", a new equivalent resonance frequency can be determined. Drive signal generator 1802 is adjusted by the controller 1830 to provide a new drive signal based on the new equivalent resonance frequency.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. An ultrasonic generator configured to supply power to an ultrasonic device, the ultrasonic generator comprising:
   a drive signal generator configured to provide a drive signal;
   an amplifier having a gain configured to amplify the drive signal;
   a noise signal generator configured to provide a noise signal;
   a resonance circuit configured to provide an output to the resonator of the ultrasonic device;
   a transformer having a first primary winding coupled to the amplifier, a second primary winding coupled to the noise signal generator and a secondary winding coupled to the resonance circuit; and
   a controller configured to:
      receive an output signal from the ultrasonic device and the noise signal from the noise signal generator,
      calculate a transfer function estimate based on the output signal and the noise signal, and
      adjust the drive signal generator based on the calculated transfer function estimate.

2. The ultrasonic generator according to claim 1, wherein the resonance circuit is an LC circuit.

3. The ultrasonic generator according to claim 1, wherein the amplifier is a Class D amplifier.

* * * * *